(12) United States Patent
Hashimoto et al.

(10) Patent No.: US 7,718,960 B2
(45) Date of Patent: May 18, 2010

(54) ION MOBILITY SPECTROMETER AND ION-MOBILITY-SPECTROMETRY/MASS-SPECTROMETRY HYBRID SPECTROMETER

(75) Inventors: Yuichiro Hashimoto, Tachikawa (JP); Hideki Hasegawa, Tachikawa (JP); Masuyuki Sugiyama, Hachioji (JP); Yasuaki Takada, Kiyose (JP)

(73) Assignee: Hitachi, Ltd., Tokyo (JP)

( * ) Notice: Subject to any disclaimer, the term of this patent is extended or adjusted under 35 U.S.C. 154(b) by 203 days.

(21) Appl. No.: 12/149,737

(22) Filed: May 7, 2008

(65) Prior Publication Data

US 2008/0277575 A1 Nov. 13, 2008

(30) Foreign Application Priority Data

May 8, 2007 (JP) ............................. 2007-122956

(51) Int. Cl.
*H01J 49/10* (2006.01)
*H01J 49/40* (2006.01)
(52) U.S. Cl. .................. 250/299; 250/281; 250/282
(58) Field of Classification Search ................. 250/286, 250/287, 288, 281, 282, 299
See application file for complete search history.

(56) References Cited

U.S. PATENT DOCUMENTS

| 4,855,595 | A * | 8/1989 | Blanchard | .................. 250/287 |
| 5,294,794 | A * | 3/1994 | Davies | ...................... 250/287 |
| 5,371,364 | A * | 12/1994 | Davies et al. | .............. 250/287 |
| 6,498,342 | B1 | 12/2002 | Clemmer | |
| 6,774,360 | B2 | 8/2004 | Guevremont et al. | |
| 7,265,345 | B2 | 9/2007 | Hashimoto et al. | |
| 2002/0014586 | A1 | 2/2002 | Clemmer | |
| 2006/0071159 | A1* | 4/2006 | Hashimoto et al. | .......... 250/287 |
| 2006/0219896 | A1* | 10/2006 | Hashimoto et al. | .......... 250/288 |
| 2007/0114382 | A1* | 5/2007 | Clemmer et al. | ............. 250/287 |
| 2007/0290128 | A1* | 12/2007 | Hashimoto et al. | .......... 250/286 |
| 2008/0251712 | A1* | 10/2008 | Sanders et al. | ............. 250/282 |
| 2008/0277575 | A1* | 11/2008 | Hashimoto et al. | .......... 250/286 |

FOREIGN PATENT DOCUMENTS

JP 2004-504696 7/2001
WO WO 02/07185 A1 7/2001

OTHER PUBLICATIONS

Siems, William et al., "Measuring the Resolving Power of Ion Mobility Spectrometers," Analytical Chemistry (Dec. 1, 1994), vol. 66, No. 23, pp. 4195-4201.

* cited by examiner

*Primary Examiner*—Bernard E Souw
(74) *Attorney, Agent, or Firm*—Stites & Harbison PLLC; Juan Carlos A. Marquez, Esq.

(57) ABSTRACT

A low-cost and high-ion-transmission-ratio ion-mobility spectrometry filter, including an ion source, a first drift region in which a gas flow direction and a DC electric-field direction are opposite to each other, a second drift region in which a gas flow direction is provided, the gas flow direction being different from the gas flow direction in the first drift region, and being opposite to a DC electric-field application direction in the second drift region, an intermediate region having an electric field for causing ions to travel between the first drift region and the second drift region, and a detector for detecting ions which have passed through the first drift region and the second drift region.

15 Claims, 4 Drawing Sheets

US 7,718,960 B2

ION MOBILITY SPECTROMETER AND ION-MOBILITY-SPECTROMETRY/MASS-SPECTROMETRY HYBRID SPECTROMETER

INCORPORATION BY REFERENCE

The present application claims priority from Japanese application JP2007-122956 filed on May 8, 2007, the content of which is hereby incorporated by reference into this application.

BACKGROUND OF THE INVENTION

1. Field of the Invention

The present invention relates to an ion mobility spectrometer and an ion-mobility-spectrometry/mass-spectrometry hybrid spectrometer.

2. Description of the Related Art

The ion mobility spectrometry is widely used for appliances such as a gas detector. Also, in addition to the ion mobility spectrometry, the mass spectrometry exists in ion detection methods. The following clear distinction, however, exists between these two methods, i.e., the ion mobility spectrometry and the mass spectrometry: In the ion mobility spectrometry, the number-of-times of collisions between ions and a gas at the time of the separation is larger in number, and rather, the effect of these collisions is taken advantage of positively. In contrast thereto, in the mass spectrometry, the number-of-times of the collisions between ions and a gas at the time of the separation is smaller in number. Namely, the ion mobility spectrometry is performed under a pressure higher than 10 mTorr; whereas the mass spectrometry is performed under a pressure lower than 1 mTorr. As a result, a significant difference therebetween is as follows: In the ion mobility spectrometry, the separation is performed based on the ion mobility; whereas, in the mass spectrometry, the separation is performed based on mass-to-charge ratios of the ions.

Hereinafter, the explanation will be given below concerning the conventional technologies. In "Analytical Chemistry", Vol. 66, No. 23, Dec. 1, 1994, pp. 4195 to 4201, the detailed description is given regarding Drift-Tube Ion Mobility Spectrometry (: DTIMS). According to this method, the attainment time of an ion to a detector is represented by the following (Expression 1), assuming that electric field is uniform, and letting ion mobility of the ion be K, voltage be V, and displacement distance be L.

$$T = \frac{L^2}{KV} \qquad \text{(Expression 1)}$$

Since the value of the ion mobility K differs depending on ion species, it is possible to separate the ion species by using the detector attainment times. The ion mobility spectrometry which takes advantage of the difference in the ion mobility like this is widely used for appliances such as an explosives detector in an airport or the like.

In U.S. Pat. No. 6,498,342 B1, the disclosure is made concerning a method where, after the ions are separated using the ion mobility, the separated ions are further detected by a mass spectrometry unit. According to this method, after the ions are separated using the ion mobility once, the mass spectrometry detection is performed by sequentially introducing the separated ions into the mass spectrometry unit such as a time-of-flight mass spectrometer. Since two-dimensional data (i.e., first-dimensional data: the ion mobility, second-dimensional data: masses of the ions) can be acquired, the resolving power is enhanced significantly.

Moreover, in U.S. Pat. No. 6,774,360 B2, the disclosure is made regarding a method of performing the ion separation by using High-Field Asymmetric-wave form Ion Mobility Spectrometry (: FAIMS). The ion mobility of the ions varies under a high electric-field strength. A filter for permitting a specific ion species to pass therethrough is implementable by using the fact that this variation ratio in the ion mobility differs depending on the ion species. The separation mechanism in U.S. Pat. No. 6,774,360 B2 differs from those in "Analytical Chemistry", Vol. 66, No. 23, Dec. 1, 1994, pp. 4195 to 4201 and U.S. Pat. No. 6,498,342 B1. This separation mechanism, however, is regarded as one type of the ion mobility spectrometry, since it is a separation mechanism performed under the atmospheric pressure or a low vacuum.

SUMMARY OF THE INVENTION

A problem occurring in "Analytical Chemistry", Vol. 66, No. 23, Dec. 1, 1994, pp. 4195 to 4201 and U.S. Pat. No. 6,498,342 B1 is that, when attention is focused on a specific ion species, the transmission efficiency is low. The ions are generated continuously in an ordinary ion source. On the other hand, the ions are introduced intermittently in the schemes of "Analytical Chemistry", Vol. 66, No. 23, Dec. 1, 1994, pp. 4195 to 4201 and U.S. Pat. No. 6,498,342 B1. As a result, ions which have passed through an acceleration region during between respective acceleration timings are lost. Accordingly, the ion transmission ratio becomes extremely low.

In U.S. Pat. No. 6,774,360 B2, in order to acquire the high electric-field strength, a high-voltage (a few kV) and high-speed (a few MHz) pulse power-source becomes necessary. As a result, there exists a problem that the filter device results in occurrence of a high cost.

An object of the present invention is to provide an ion-mobility spectrometry method which allows implementation of a low cost and a high ion transmission ratio.

Another object of the present invention is to provide a low-cost and high-ion-transmission-ratio ion-mobility spectrometry filter for permitting ions of a specific range of ion mobility to pass therethrough under the atmospheric pressure.

An ion mobility spectrometer of the present invention includes an ion source, a first drift region in which a gas flow direction and a DC electric-field direction are opposite to each other, a second drift region in which a gas flow direction is provided, the gas flow direction being different from the gas flow direction in the first drift region, and being opposite to a DC electric-field application direction in the second drift region, an intermediate region having an electric field for causing ions to travel between the first drift region and the second drift region, and a detector for detecting ions which have passed through the first drift region and the second drift region.

Moreover, in the ion mobility spectrometer of the present invention, the gas is caused to flow from the intermediate region to each of the first drift region and the second drift region.

Furthermore, in the ion mobility spectrometer of the present invention, the gas is caused to flow from each of the first drift region and the second drift region to the intermediate region.

Also, an ion-mobility-spectrometry/mass-spectrometry hybrid spectrometer of the present invention includes an ion source, a drift region having a gas flow direction and a DC electric-field direction, the gas flow direction being identical to an ion traveling direction, the DC electric-field direction being opposite to the ion traveling direction, and a mass spectrometer for detecting ions which have passed through the drift region, wherein the gas flow in the drift region satisfies a laminar-flow condition.

According to the present invention, it becomes possible to implement the low-cost and high-ion-transmission-ratio ion-mobility spectrometry filter for permitting the ions of a specific range of ion mobility to pass therethrough under the atmospheric pressure.

Other objects, features and advantages of the invention will become apparent from the following description of the embodiments of the invention taken in conjunction with the accompanying drawings.

DETAILED DESCRIPTION OF THE INVENTION

1st Embodiment

Figure 1:
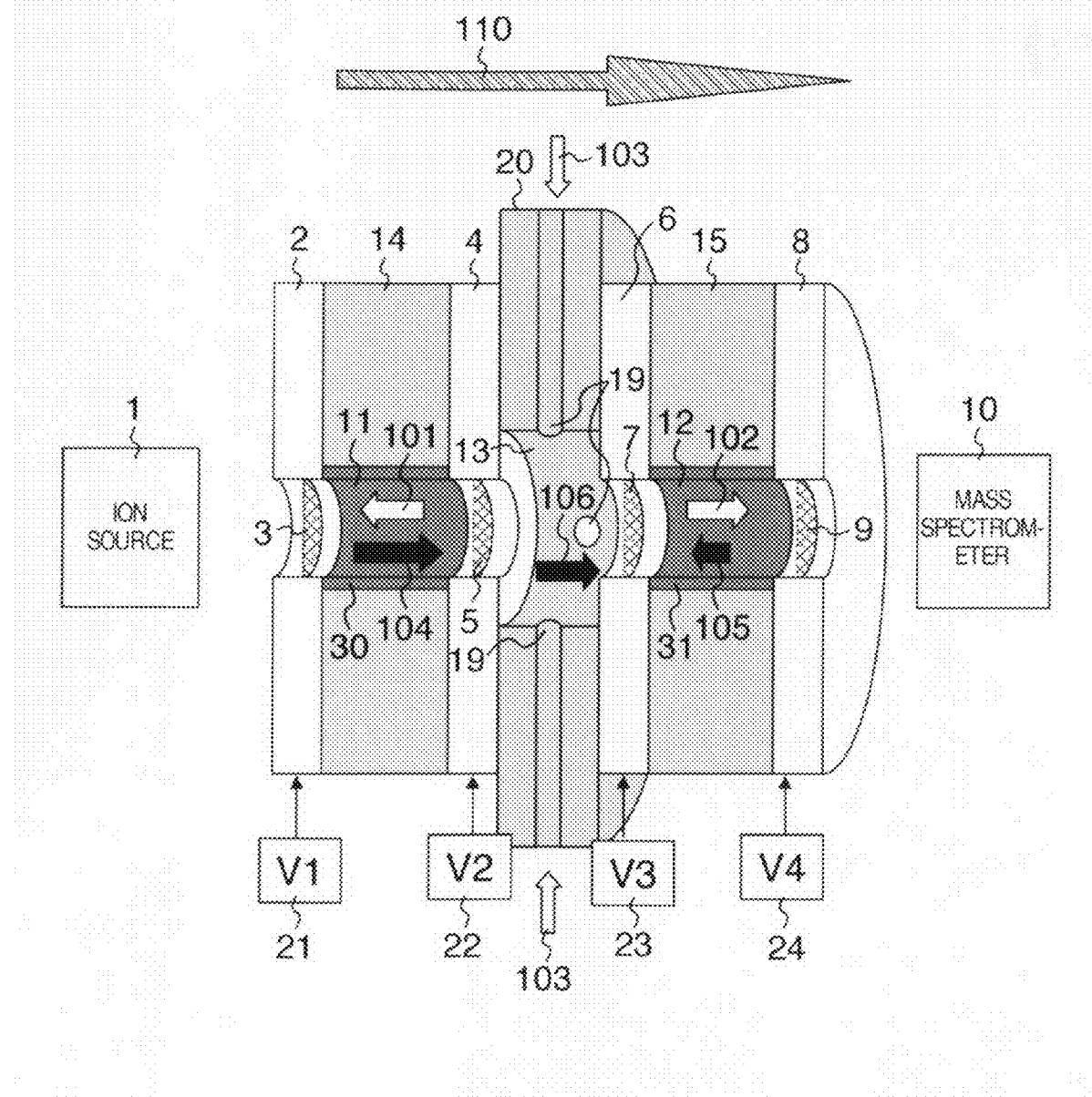
FIG. 1 illustrates a first embodiment of the present scheme.

FIG. 1 is a configuration diagram of an ion mobility spectrometer in which the present scheme is carried out. First, ions are generated by an atmospheric-pressure ion source 1, such as atmospheric-pressure chemical ion source, electrospray ion source, and atmospheric-pressure matrix-assisted laser desorption ion source. Next, the ions generated pass through a small orifice (substantially 0.1 mmφ to 10 mmφ, which is denoted by D) of a first inlet electrode 2, then being introduced into a first drift region 11. The first drift region 11 is surrounded by the first inlet electrode 2 and a first exit electrode 4. Here, the ion source is not limited to the atmospheric-pressure ion source, but whatever ion source is available as long as it can ionize the sample. The first drift region 11 is equal to substantially 1 mm to 100 mm in length.

In the first drift region 11, there occurs a velocity vector 104, which is caused to occur towards the ions in an ion traveling direction 110 by an electric field. In order to form this traveling velocity vector 104 based on the electric field, a DC voltage is applied to the first inlet electrode 2 and the first exit electrode 4 by a power-supply 21 and a power-supply 22, respectively. As the electric-field strength $E_1$ in the first drift region 11, a substantially 10-V/m to 100-V/m electric-field strength is applied. Incidentally, the ion mobility K, which differs depending on ion species, has a value of substantially 100 mm$^2$/Vs to 300 mm$^2$/Vs. As a result, when the electric-field strength $E_1$ in the first drift region 11 is equal to, e.g., 30 V/m, there occurs the velocity vector 104 whose velocity absolute-value is equal to $KE_1$, i.e., 3 m/s to 9 m/s, and which differs depending on the ion species. In order to form a parallel electric field in the first drift region 11, it is desirable to set up mesh electrodes 3 and 5 in the small orifice of the first inlet electrode 2 and a small orifice of the first exit electrode 4, respectively.

Also, electrical insulation is established between the first inlet electrode 2 and the first exit electrode 4 by using an insulating spacer 14. At this time, the electric-field uniformity in the first drift region 11 can be improved even further by applying an electrically-conductive coating 30 onto the inner wall. The higher the electrically-conductive degree of the coating 30 becomes, the less likely it becomes that charge-up will occur. This is truly an advantage that does exist; however, there also occur such problems as heat-liberation and resultant large-sized formation of the power-supplies due to an increase in the electric current. In view of this situation, the coating method is adjusted so that resistance value between the first inlet electrode 2 and the first exit electrode 4 falls in a range of $10^3 \Omega$ to $10^6 \Omega$. The use of a metal oxide such as ITO or $ZnO_2$ as the coating method allows high-temperature implementation of the drift region by a (not-illustrated) heater. The high-temperature implementation of the drift region makes it possible to improve the problem of adherence of dirt.

On the other hand, in the first drift region 11, a gas flow 101 (whose velocity is assumed to be $U_1$) is made to flow in a direction opposite to the ion traveling direction 110. When the electric field is absent, this set-up of the gas flow causes the ions to travel in accordance with this velocity vector ($U_1$). Incidentally, in order to uniformalize the traveling velocity of the ions by the gas in the first drift region 11, a laminar-flow condition needs to be satisfied. As the criterion for the laminar-flow condition, it is preferable to use a condition that Reynolds number Re represented by the following (Expression 2) becomes smaller than 2000.

$$Re = \frac{U_1 D}{v} \quad \text{(Expression 2)}$$

Here, $v$ denotes kinematic viscosity coefficient (which is equal to $1.583 \times 10^{-5}$ m$^2$/s in the 300-K air). For example, when letting the diameter D of the first drift region 11 be 3 mm, and the gas-flow velocity $U_1$ be 5 m/s, it turns out that Re=950. This means that the laminar-flow condition is satisfied. When considering the gas-flow velocity $U_1$ and the above-described electric-field-based velocity vector 104 (whose velocity is equal to $KE_1$) simultaneously, it turns out that only an ion species which satisfies the following (Expression 3) has a velocity vector in the ion traveling direction 110 in the first drift region 11, and can pass through the first drift region 11.

$$KE_1 > U_1 \quad \text{(Expression 3)}$$

The ions which have passed through the first drift region 11 are then introduced into an intermediate region 13 which is surrounded by the first exit electrode 4 and a second inlet electrode 6. In the intermediate region 13, an electric field 106 is caused to occur between the first exit electrode 4 and the second inlet electrode 6. This occurrence of the electric field 106 causes the ions to travel in the ion traveling direction 110. Also, the gas such as dried air or nitrogen gas is introduced into this portion in a gas-introducing direction from a gas-introducing orifice 19. This gas will be introduced into the first drift region 11 described earlier and a second drift region 12 which will be described later.

The ions introduced from the intermediate region 13 pass through a small orifice (substantially 0.1 mmφ to 5 mm) of the second inlet electrode 6, then being introduced into the second drift region 12 which is surrounded by the second inlet electrode 6 and a second exit electrode 8. The second drift region 12 is equal to substantially 1 mm to 100 mm in length. In the second drift region 12, a velocity vector 105, which is caused to occur towards the ions by an electric field, is formed in a direction opposite to the ion traveling direction 110. In order to form this electric-field-based velocity vector 105, a DC voltage is applied to the second inlet electrode 6 and the second exit electrode 8 by a power-supply 23 and a power-supply 24, respectively. As the electric-field strength $E_2$ in the second drift region 12, a substantially 10-V/m to 100-V/m electric-field strength is applied.

Incidentally, the ion mobility K, which differs depending on the ion species, has the value of substantially 100 mm²/Vs to 300 mm²/Vs. As a result, when the electric-field strength $E_2$ in the second drift region 12 is equal to, e.g., 20 V/m, the ions undergo the traveling velocity vector 105 in the direction opposite to the ion traveling direction 110. At this time, the velocity absolute-value of the velocity vector 105 is equal to $KE_2$, i.e., 2 m/s to 6 m/s, and differs depending on the ion species. In order to form a parallel electric field in the second drift region 12, it is desirable to set up mesh electrodes 7 and 9 in the small orifice of the second inlet electrode 6 and a small orifice of the second exit electrode 8, respectively.

Also, electrical insulation is established between the second inlet electrode 6 and the second exit electrode 8 by using an insulating spacer 15. At this time, the electric-field uniformity in the second drift region 12 can be improved by applying an electrically-conductive coating 31 onto the inner wall. Details of the coating are similar to those in the first drift region 11, and thus will be omitted.

On the other hand, in the second drift region 12, a gas flow 102 (whose velocity is assumed to be $U_2$) is made to flow in the direction identical to the ion traveling direction 110. When the electric field is absent, this set-up of the gas flow causes the ions to travel in accordance with this velocity vector ($U_2$) in the ion traveling direction 110. Incidentally, it is desirable that the above-described laminar-flow condition be satisfied in the second drift region 12 as well. When considering the gas-flow velocity $U_2$ and the above-described electric-field-based velocity vector 105 (whose velocity is equal to $KE_2$) simultaneously, it turns out that only an ion species which satisfies the following (Expression 4) has a velocity vector in the ion traveling direction 110 in the second drift region 12, and can pass through the second drift region 12.

$$KE_2 < U_2 \quad \text{(Expression 4)}$$

From the foregoing explanation, only an ion species which satisfies the following (Expression 5) can pass through the first and second drift regions 11 and 12.

$$\frac{U_1}{E_1} < K < \frac{U_2}{E_2} \quad \text{(Expression 5)}$$

The ions which have passed through the first and second drift regions 11 and 12 are then introduced into a detector or an in-vacuum mass spectrometer 10. Here, the ions are detected after the mass separation is performed.

Figure 2:
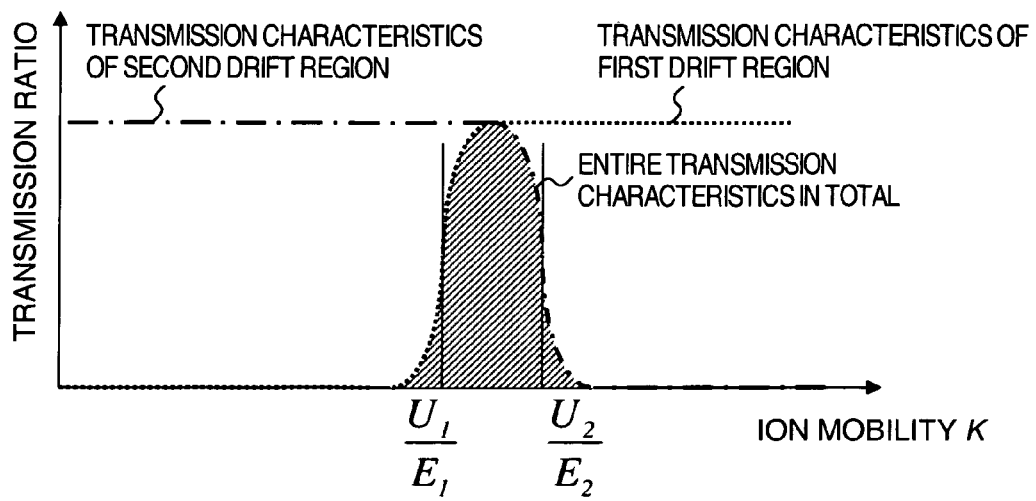
FIG. 2 is an explanatory diagram for explaining effects of the present scheme.

FIG. 2 illustrates transmission characteristics of the ion species each of which has the different ion mobility K in the case indicated in the first embodiment. The horizontal axis denotes the ion mobility, and the vertical axis denotes the ion transmission. In the first drift region 11, as indicated by the dotted line, only ions whose ion mobility is higher than a certain specific value can pass therethrough. Meanwhile, in the second drift region 12, as indicated by the alternate long-and-short dashed line, only ions whose ion mobility is lower than a certain specific value can pass therethrough. As a consequence, as a whole, the ion mobility spectrometer functions as an ion-mobility spectrometry filter for permitting only ions having a specific range of ion mobility to pass therethrough not intermittently but continuously. As a result, the ion transmission ratio becomes high.

Figure 3A:
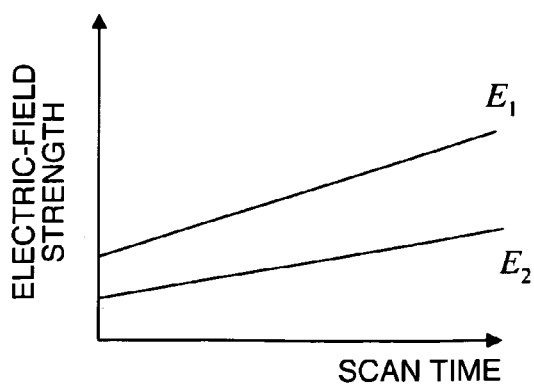
FIG. 3A and FIG. 3B illustrate measurement sequences in the first embodiment.
Figure 3B:
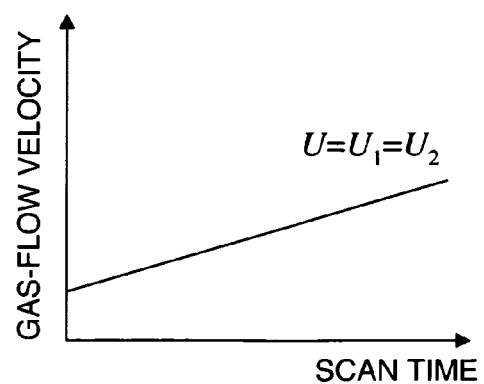

Also, as illustrated in FIG. 3A and FIG. 3B, the electric-field strengths and the gas-flow velocities in the first drift region and the second drift region are varied in time. This varying operation makes it possible to scan the values of the ion mobility which are permitted to pass through the first and second drift regions. When the values are scanned as are illustrated in FIG. 3A and FIG. 3B, it turns out that the ions pass therethrough in different time-zones. This is because the values of the ion mobility K differ depending on the ion species. Namely, in FIG. 3A, the electric-field strengths are varied in time. This varying operation shifts the transmission condition from the ion having a lower mobility to the ion having a higher mobility. In FIG. 3B, the gas-flow velocities are varied in time. This varying operation shifts the transmission condition from the ion having a lower mobility to the ion having a higher mobility. Also, the first drift region and the second drift region are configured using basically the same configuration components, thereby making conductances of the gas flows equal to each other. This operation allows the gas-flow velocities to be set at an equal gas-flow velocity (i.e., $U_1 = U_2$). In this case, there exists an effect that the cost can be reduced by the unification of the configuration components.

2nd Embodiment

Figure 4:
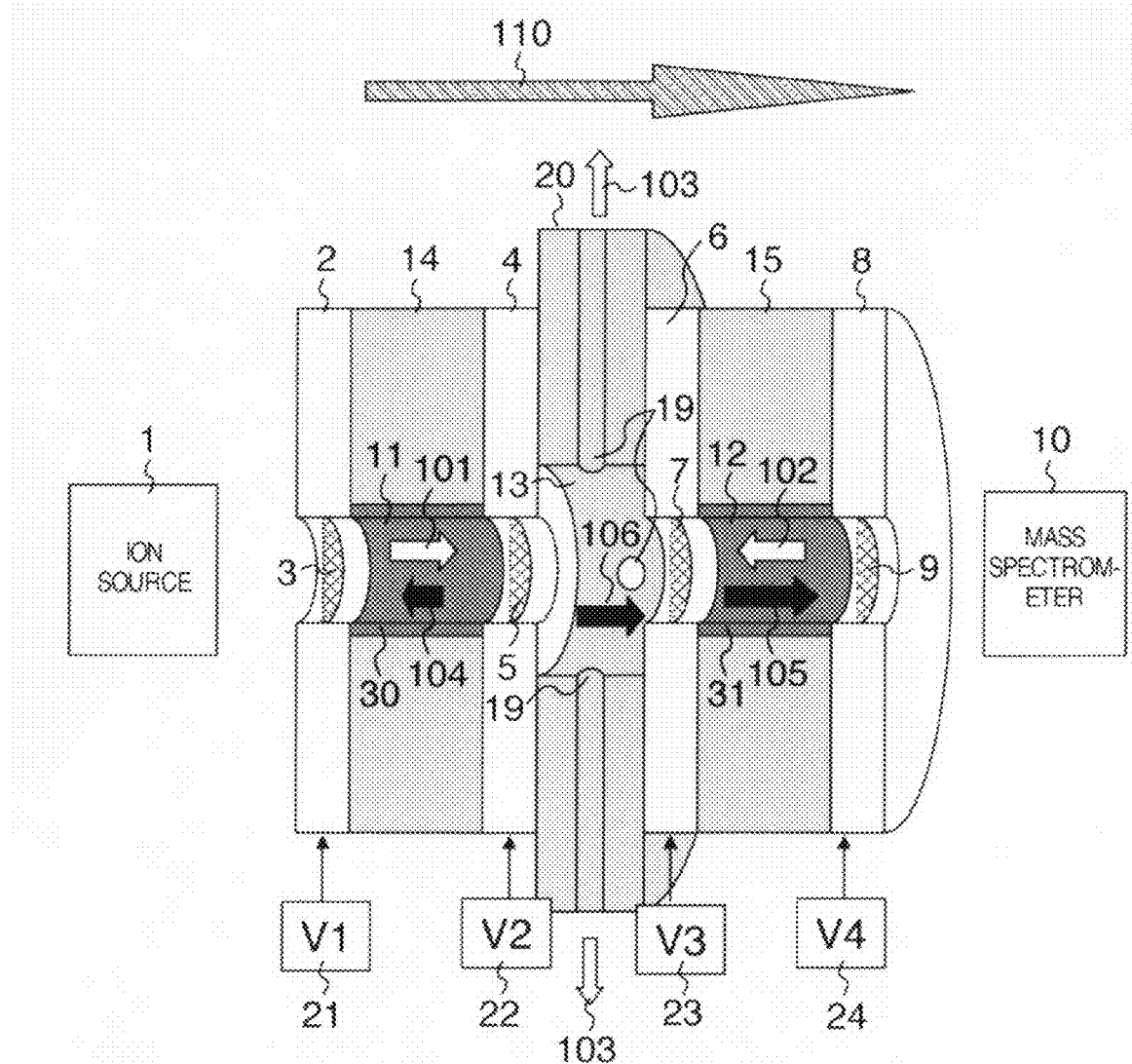
FIG. 4 illustrates a second embodiment of the present scheme.
Figure 5:
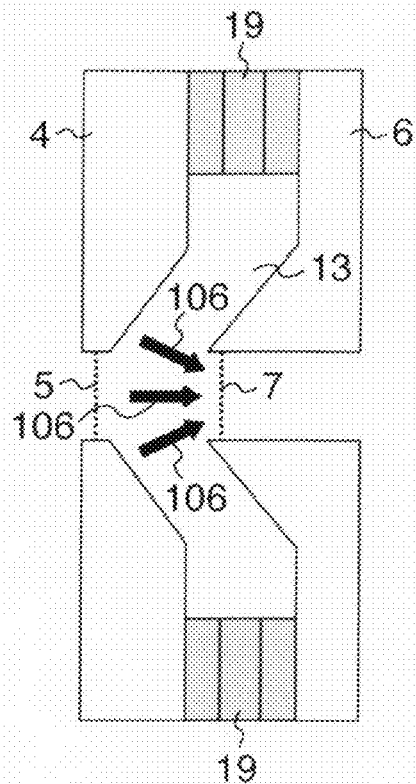
FIG. 5 illustrates the second embodiment of the present scheme.

FIG. 4 illustrates a second embodiment of the present invention. In the second embodiment, the ions generated from the ion source are sent to the detector or the in-vacuum mass spectrometer 10 via the first drift region 11 and the second drift region 12. This process is basically the same as the one in the first embodiment. In the second embodiment, however, the gas-flow direction in each drift region is opposite to the one in the first embodiment. Concretely, the gas is pumped in the direction indicated by 103, using a (not-illustrated) pump. Also, in accompaniment with the changes in the gas-flow directions, the direction and strength of each electric field differ from the ones in the first embodiment. In the second embodiment, only an ion which satisfies the following (Expression 6) can pass through the first drift region 11, and only an ion which satisfies the following (Expression 7) can pass through the second drift region 12. As a consequence, only an ion which satisfies the following (Expression 8) can pass through the first drift region 11 and the second drift region 12, then attaining to the detector or the in-vacuum mass spectrometer 10.

$$KE_1 < U_1 \quad \text{(Expression 6)}$$

$$KE_2 > U_2 \quad \text{(Expression 7)}$$

$$\frac{U_2}{E_2} < K < \frac{U_1}{E_1} \quad \text{(Expression 8)}$$

Incidentally, as a problem common to the first embodiment and the second embodiment, there exists the problem of a lowering in the ion transmission ratio in the intermediate region 13. The reason for this lowering is that a turbulent flow of the gas flow is generated in a portion of the intermediate region 13. In order to compensate for this decrease in the ion transmission, it is desirable to use a configuration illustrated in FIG. 4 in the intermediate region 13. Namely, the first exit electrode 4 and the second inlet electrode 6 are machined and formed into a taper-like configuration. This taper-like configuration gives rise to occurrence of an electric-field vector 106 oriented in the central direction, thereby resulting in an effect that the ions will be converged into the central portion. This effect allows implementation of an enhancement in the ion transmission ratio in the intermediate region 13.

3rd Embodiment

Figure 6:
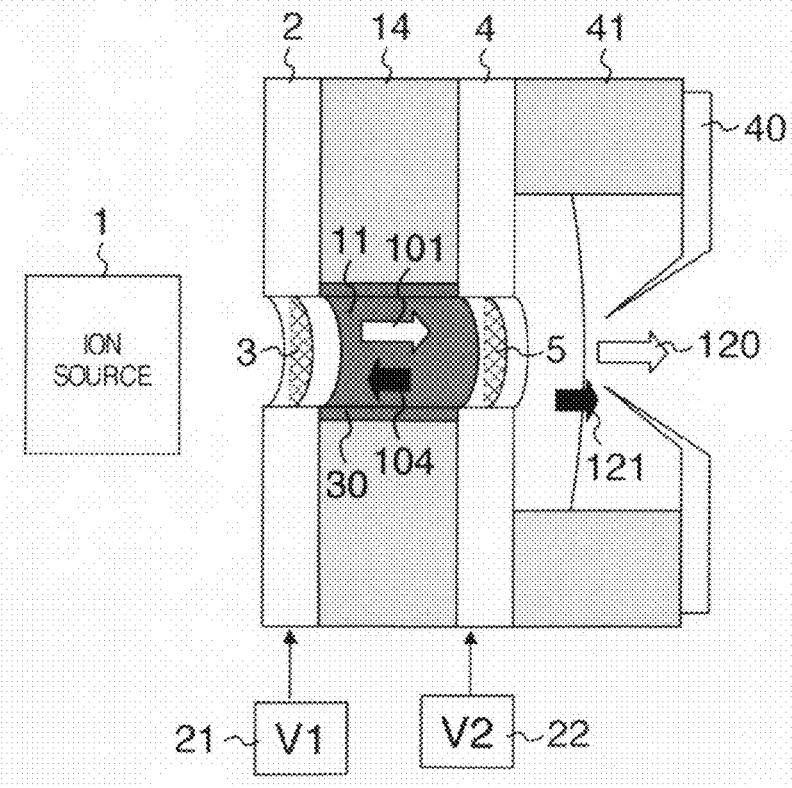
FIG. 6 illustrates a third embodiment of the present scheme.

The foregoing embodiments are the embodiments where the two drift regions having the mutually different electric-field directions are arranged in series. FIG. 6 illustrates a third embodiment where the ion mobility spectrometer is combined with the mass spectrometer. In the mass spectrometer, the ions can be separated based on differences in the masses. As a result, as the ion mobility spectrometer which is the preceding-stage spectrometer to the mass spectrometer, only the coarse separation is required in some cases. In the first and second embodiments, the ions having a specific range (its upper-limit value and lower-limit value exist) of ion mobility have been permitted to pass therethrough. In the present embodiment, however, the explanation will be given below concerning an example of the ion-mobility spectrometry filter in the first drift region 11 alone.

Of the ions generated by the ion source 1, only the ions whose ion mobility is lower than a certain specific value can pass through the first drift region 11. This process is basically the same as the one in the second embodiment. In the present embodiment, however, the gas flow 101 is caused to occur by a gas introduction 120 into the mass spectrometry unit. Accordingly, there exists a merit of being capable of reducing the cost for setting up the pump separately as in the second embodiment. In the first drift region 11, the ions having the lower ion mobility can pass therethrough. The ions which have passed through the first drift region 11 are displaced in a direction 121 by an electric field applied between the first exit electrode 4 and a first small orifice 40 of the mass spectrometer. Moreover, from the first small orifice 40, the ions are introduced into the mass spectrometry unit, where the mass spectrometry detection is performed by various mass-spectrometry units. Incidentally, for the purpose of gas sealing, an insulating spacer 41 such as ceramic is set up between the first exit electrode 4 and the first small orifice 40. Also, as is the case with the first and second embodiments, in order to form a parallel electric field in the first drift region 11, it is desirable to set up the mesh electrodes 3 and 5 in the small orifice of the first inlet electrode 2 and the small orifice of the first exit electrode 4, respectively.

Incidentally, although this method is the one common to the first to the third embodiments, in the present embodiment as well, the example of coating the electrical conductor on the inner wall of the ceramic is described as the method for applying the uniform electric field to the first drift region 11. Basically the same effect, however, can also be accomplished in a case where the electrically-conductive property is implemented by doping the ceramic or plastic itself with the electrically-conductive substance, or a case where a plurality of metallic electrodes are arranged with a resistor placed therebetween. Also, only the case where the first drift region 11 and the second drift region 12 are arranged in series on the coaxial axis has been described in the first and second embodiments. Basically the same effect, however, can also be expected in a structure where the direction of the first drift region 11 and the direction of the second drift region 12 wind and curve to each other or are orthogonal to each other. In this case, there exists a demerit that the structure becomes complicated. On the other hand, there also exists a merit that noise due to the straight-traveling particles can be reduced, since sight angle from the ion source to the detector is reduced.

In the spectrometer of the present invention, unlike the spectrometers in "Analytical Chemistry", Vol. 66, No. 23, Dec. 1, 1994, pp. 4195 to 4201 and U.S. Pat. No. 6,498,342 B1, the continuous ion introduction is executable. This feature allows implementation of the high ion transmission ratio. Also, unlike U.S. Pat. No. 6,774,360 B2, the spectrometer of the present invention can be configured using the low-cost DC power-supplies alone. This feature makes it possible to fabricate the spectrometer at a low cost.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An ion mobility spectrometer, comprising:
   an ion source;
   a first drift region in which a gas flow direction and a DC electric-field direction are opposite to each other;
   a second drift region in which a gas flow direction is provided, said gas flow direction being different from said gas flow direction in said first drift region, and being opposite to a DC electric-field application direction in said second drift region;
   an intermediate region having an electric field for causing ions to travel between said first drift region and said second drift region; and
   a detector for detecting ions which have passed through said first drift region and said second drift region.

2. The ion mobility spectrometer according to claim 1, wherein
   said gas is caused to flow from said intermediate region to each of said first drift region and said second drift region.

3. The ion mobility spectrometer according to claim 1, wherein
   said gas is caused to flow from each of said first drift region and said second drift region to said intermediate region.

4. The ion mobility spectrometer according to claim 1, wherein
   said gas flow in said first drift region and said gas flow in said second drift region satisfy a laminar-flow condition.

5. The ion mobility spectrometer according to claim 1, wherein said detector is a mass spectrometer.

6. The ion mobility spectrometer according to claim 1, wherein said detector is an electric-current measuring instrument.

7. The ion mobility spectrometer according to claim 1, wherein said ion source is an atmospheric-pressure ion source.

8. The ion mobility spectrometer according to claim 1, wherein
   electric-field generating means in at least either of said first drift region and said second drift region uses electrically-conductive coating.

9. The ion mobility spectrometer according to claim 1, wherein
   an electrode facing said intermediate region is machined and formed into a taper-like configuration.

10. The ion mobility spectrometer according to claim 1, wherein
a mesh electrode is provided at an inlet end and an exit end of at least one of said first drift region and said second drift region.

11. The ion mobility spectrometer according to claim 1, wherein
value of said ion mobility is scanned by varying, in time, at least either of said gas and said electric field in each of said first drift region and said second drift region.

12. An ion-mobility-spectrometry/mass-spectrometry hybrid spectrometer, comprising:
an ion source;
a drift region having a gas flow direction and a DC electric-field direction, said gas flow direction being identical to an ion traveling direction, said DC electric-field direction being opposite to said ion traveling direction; and
a mass spectrometer for detecting ions which have passed through said drift region; wherein
said gas flow in said drift region satisfies a laminar-flow condition.

13. The ion-mobility-spectrometry/mass-spectrometry hybrid spectrometer according to claim 12, wherein
said ions are introduced into said mass spectrometer by applying an electric field between an exit electrode of said drift region and an ion-introducing orifice of said mass spectrometer.

14. The ion-mobility-spectrometry/mass-spectrometry hybrid spectrometer according to claim 12, wherein
electric-field generating means in said drift region uses electrically-conductive coating.

15. The ion-mobility-spectrometry/mass-spectrometry hybrid spectrometer according to claim 12, wherein
a mesh electrode is used at least one of at an inlet end and at an exit end of said drift region.

* * * * *